United States Patent

Houser et al.

[11] Patent Number: 6,063,318
[45] Date of Patent: *May 16, 2000

[54] METHOD OF FORMING A CATHETER BODY FROM TUBING SEGMENTS

[75] Inventors: Russell A. Houser, Livermore; Jerome Jackson, Sunnyvale; Russell B. Thompson, Meno Park, all of Calif.

[73] Assignee: EP Technologies, Inc., San Jose, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/681,666

[22] Filed: Jul. 29, 1996

Related U.S. Application Data

[62] Division of application No. 08/561,092, Nov. 21, 1995, Pat. No. 5,569,221, which is a continuation of application No. 08/271,186, Jul. 7, 1994, abandoned.

[51] Int. Cl.[7] .................................................. B29C 65/02
[52] U.S. Cl. .................. 264/248; 156/304.2; 156/304.3; 156/304.6
[58] Field of Search .................................. 264/248, 449; 156/304.2, 304.3, 304.6

[56] References Cited

U.S. PATENT DOCUMENTS

| | | |
|---|---|---|
| 2,472,484 | 6/1949 | Krippendorf . |
| 2,472,485 | 6/1949 | Krippendorf . |
| 3,094,452 | 6/1963 | Riegen et al. ............................ 264/449 |
| 3,308,523 | 3/1967 | Ivester et al. ............................. 29/127 |
| 3,416,531 | 12/1968 | Edwards . |
| 3,485,234 | 12/1969 | Stevens . |
| 3,660,192 | 5/1972 | Smith et al. ........................... 156/304.2 |
| 3,879,516 | 4/1975 | Wolvek .................................... 264/264 |
| 3,924,632 | 12/1975 | Cook . |
| 4,516,972 | 5/1985 | Samson . |
| 4,563,181 | 1/1986 | Wijayarathna et al. . |
| 4,636,346 | 1/1987 | Gold et al. . |
| 4,690,175 | 9/1987 | Ouchi et al. . |
| 4,735,620 | 4/1988 | Ruiz . |
| 4,817,613 | 4/1989 | Jaraczewski et al. . |
| 4,842,590 | 6/1989 | Tanabe et al. . |
| 4,863,442 | 9/1989 | DeMello et al. . |
| 4,899,787 | 2/1990 | Ouchi et al. . |
| 4,927,642 | 5/1990 | Kunz ....................................... 264/248 |
| 4,955,862 | 9/1990 | Sepetka . |
| 4,969,972 | 11/1990 | Kunz ....................................... 264/248 |
| 5,037,404 | 8/1991 | Gold et al. . |
| 5,254,107 | 10/1993 | Soltesz . |
| 5,257,451 | 11/1993 | Edwards et al. . |

FOREIGN PATENT DOCUMENTS

| | | |
|---|---|---|
| WO91/13648 | 9/1991 | WIPO . |
| WO91/17782 | 11/1991 | WIPO . |

*Primary Examiner*—Jan H. Silbaugh
*Assistant Examiner*—Edmund H. Lee
*Attorney, Agent, or Firm*—Lyon & Lyon LLP

[57] ABSTRACT

A method of bonding sections of a catheter body together in abutting relationship including the steps of providing a temperature resistance polymeric sleeve, which sleeve preferably has a spirally wound metallic wire imbedded between its inner and outer diameters. The sleeve is inserted into ends of tubing segments to be joined together to form a catheter body. Then heat is applied over the area including the sleeve to melt the tubing over the sleeve.

7 Claims, 3 Drawing Sheets

METHOD OF FORMING A CATHETER BODY FROM TUBING SEGMENTS

This is a divisional of application(s) Ser. No. 08/561,092, filed on Nov. 21, 1995, now U.S. Pat. No. 5,569,221 which is a continuation of application of Ser. No. 08/271,186 filed Jul. 7, 1994, now abandoned.

FIELD OF THE INVENTION

This invention relates to medical devices such as intravascular catheters. More specifically, the invention relates to such catheters that can be steered and manipulated in interior regions of the body by means of a control mechanism located outside of the body, and to improved bonding together of the components thereof.

BACKGROUND OF THE INVENTION

Catheters for use in medical procedures have come into widespread use. Particularly critical in terms of required strength and flexibility are catheters used for procedures such as electrophysiological therapy of the heart, for example in measurement of electrical activity within the heart and/or ablation of tissue for treatment of cardiac rhythm disturbances.

During these procedures, a physician steers a catheter through a blood vessel into the chamber of the heart that is to be treated. Steering wires extending into the catheter are provided in order to allow precise bending and steering of the catheter. It is, thus, important that the bonds between various components of the catheter have the integrity sufficient to withstand the necessary bending, twisting and tensile forces.

Heretofore, it has been common to form the bonds between catheter components such as between the catheter body and distal tip components by means of either adhesive bonds or by thermal bonds formed by melting of the materials of construction of the catheter components. See, for example, U.S. Pat. No. 5,254,107 issued to Soltesz on Oct. 19, 1993. A need has continued to exist for improved bonding methods and structures for such catheters.

SUMMARY OF THE INVENTION

The invention provides an improved flexible bond between abutting segments of a catheter. Specifically, the invention provides a method of forming a bond joint between segments of a catheter having varying physical properties. An important aspect of the present invention is to provide a bonding technique that provides a stronger, yet flexible, tubing bond between abutting components of a catheter body that are formed from dissimilar materials such as different durometer plastic tubing. Also, connection of a catheter body tubing that contains metal reinforcement to an unreinforced section of tubing, such as the catheter distal tip, is facilitated by the present invention.

A further important aspect of the invention is the provision of a construction of materials thermally bonded together that, as a composite, has exceptional tensile strength. In accordance with a preferred embodiment of the invention, a heat resistant polymeric tubing material such as a polyamide polymer, reinforced by a spirally wrapped metal reinforcing wire, is utilized as a bonding element in a joint between two catheter components or segments.

Another important aspect and object of the invention is to provide a method wherein thermal bonding of catheter components into an abutting relationship is achieved without the requirement that a mandrel be used within the catheter during the thermal bonding step. A further aspect of the invention is to provide a joint having the components thermally bonded in abutting relationship with high tensile strength enhanced by the profile of a spirally wrapped metallic reinforcement.

Briefly, the invention provides a method of bonding sections of a catheter body together in abutting relationship including the steps of providing a temperature resistant polymeric sleeve, which sleeve preferably has a spirally wound metallic wire imbedded between its inner and outer diameters. The sleeve is inserted into ends of tubing segments to be joined together to form a catheter body. Then heat is applied over the area including the sleeve to melt the tubing over the sleeve thereby bonding the segments together.

DETAILED DESCRIPTION OF PREFERRED EMBODIMENTS

Figure 1:
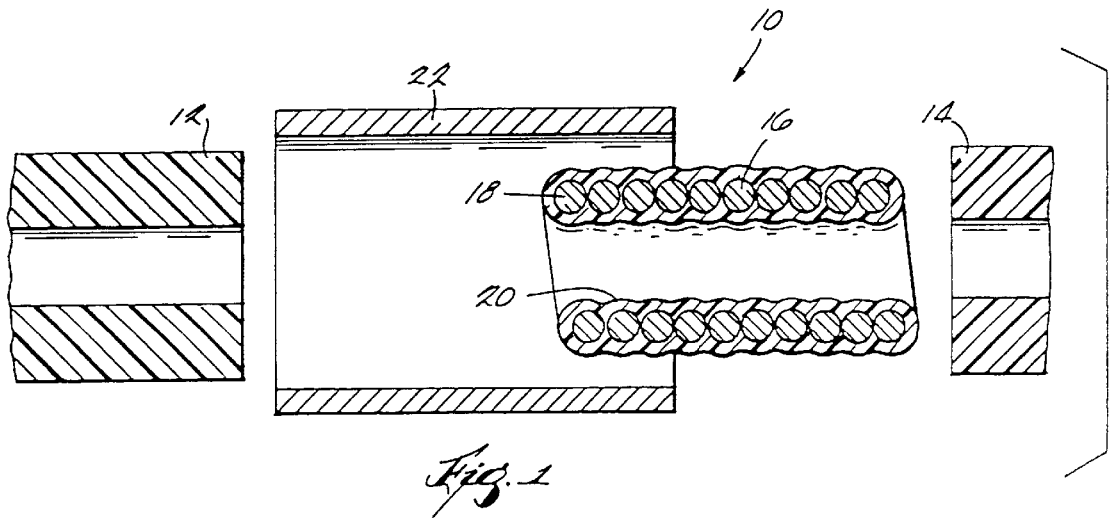
FIG. 1 is a central cross-sectional view showing two catheter segments to be joined and a sleeve used in joining them.

Referring more particularly to the drawings, there are shown in the various views, a catheter body 10 formed of at least two segments 12 and 14. A sleeve 16, which includes a spirally wound round cross sectioned metal wire reinforcement 18 is used to join together segments 12 and 14.

Segments 12 and 14 may be dissimilar materials. For example, one section intended as a catheter body may be formed of Pebax, a copolymer of polyamide and polyester (available from Rilsan), which is often reinforced by means of a braided metal tube. The other segment may be, for example, a polyurethane elastomer. A preferred material for the body 20 of sleeve 16 is a polyamide polymer, which has a substantially higher melting point (or transition temperature, i.e., about 700° F.) than the materials forming the segments 12 and 14. In case of the noted examples, Pebax reaches a flowable consistency at 370° F., a representative polyurethane elastomer at about 320° F., and a polyamide at about 700° F.

In practice, it is preferred that a spirally wound metal reinforcement 18 be positioned between the inner and outer diameters of the material of tube 16. As noted, the surfaces of tube 16 are provided with a somewhat undulating surface due to the presence of reinforcing wire 18, which may be of any desired cross section. This undulating configuration is believed to assist greatly in producing a bonded catheter body which has excellent tensile strength after melting into the undulations of the materials being bonded.

Figure 2:
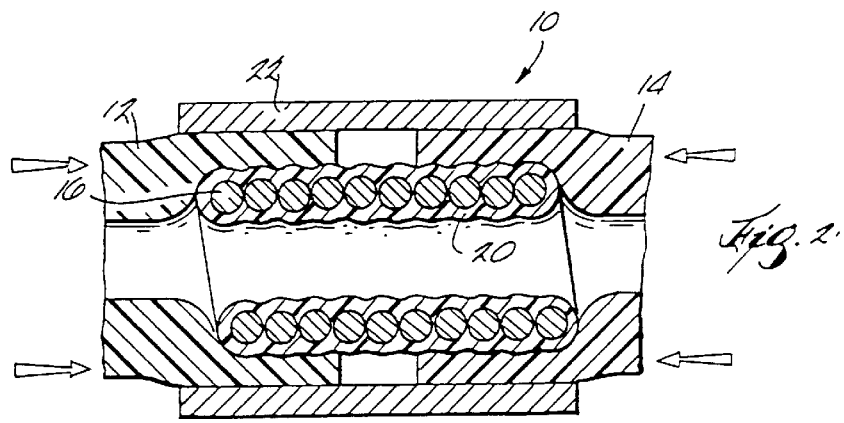
FIG. 2 is a cross-sectional view showing the components of FIG. 1 being positioned together in a supporting tube for heating.

As seen in FIG. 2, it is preferred that the assembly be placed within a capture tube 22 which serves as a mold. Such placement is best effected by pushing the two ends toward each other, for example by finger pressure, while heating the assembly, for example, by using a flow of heated air to soften the materials. Longitudinal pressure is thus applied equally to segments 12 and 14 to cause flow of the softening materials about the sleeve 16. About 1 to 2 pounds of pressure is applied at each end.

Capture tube 22 is preferably formed of polytetrafluroethylene (PTFE). PTFE retains its structural integrity to temperatures over 700° F.

Figure 3:
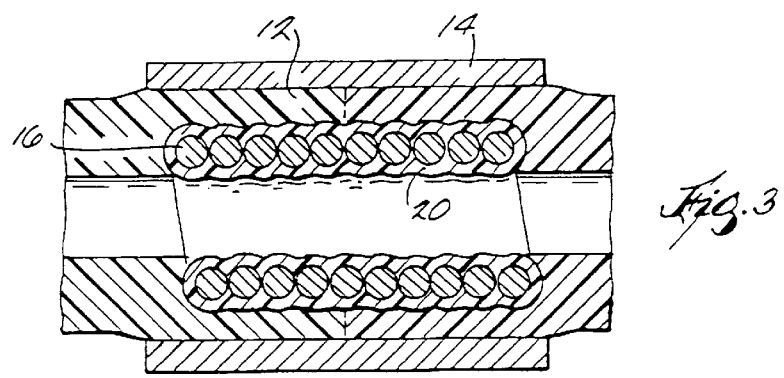
FIG. 3 is a cross-sectional view of the components of FIG. 1 after they have been bonded together.
Figure 4:
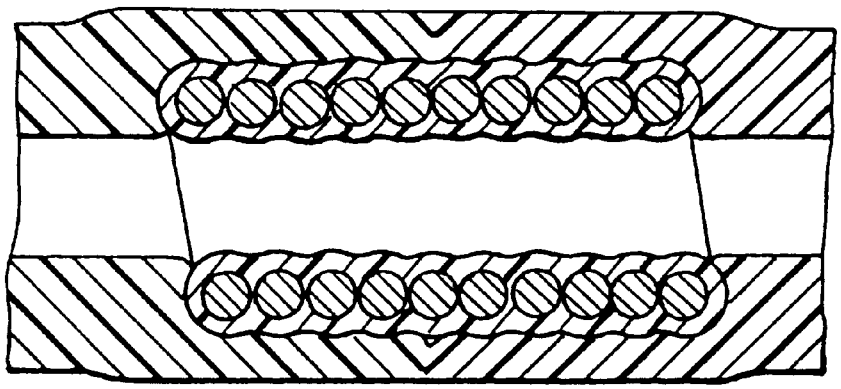
FIG. 4 is a cross-sectional view showing the sections of FIG. 3 after removal from the supporting tube.

The assembly shown in FIG. 2 is heated either by placement thereof in a heating die or by applying a stream of heated air to the surface. The heating raises the materials forming segments 12 and 14 above their melting points, but the melting point of material 16 forming the body of sleeve 20 is not attained. Thus, the materials flow together to give the reinforced butt bond configuration illustrated in FIGS. 3 and 4.

Figure 5:
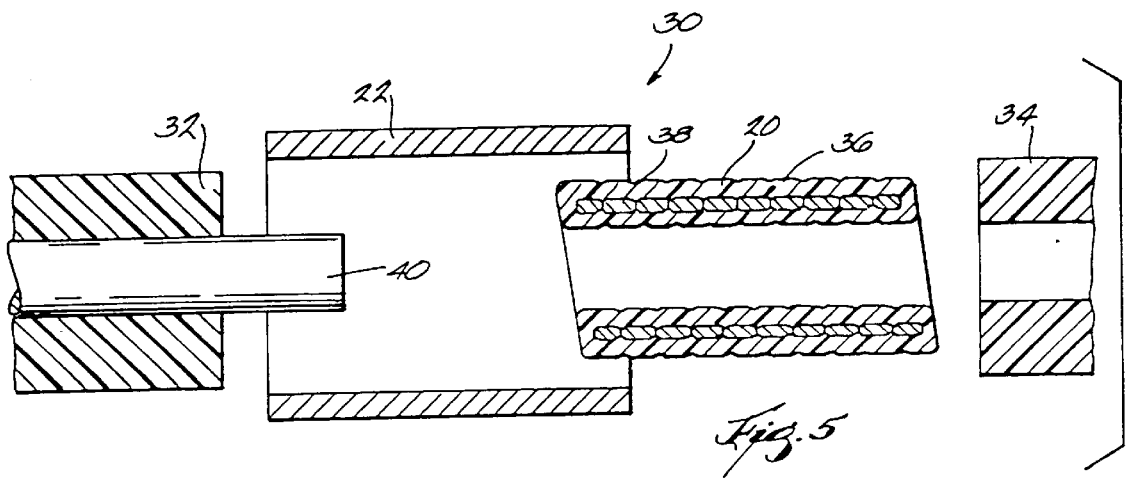
FIG. 5 shows a different embodiment of the invention with tube sections to be joined together in a sleeve and over a mandril.
Figure 6:
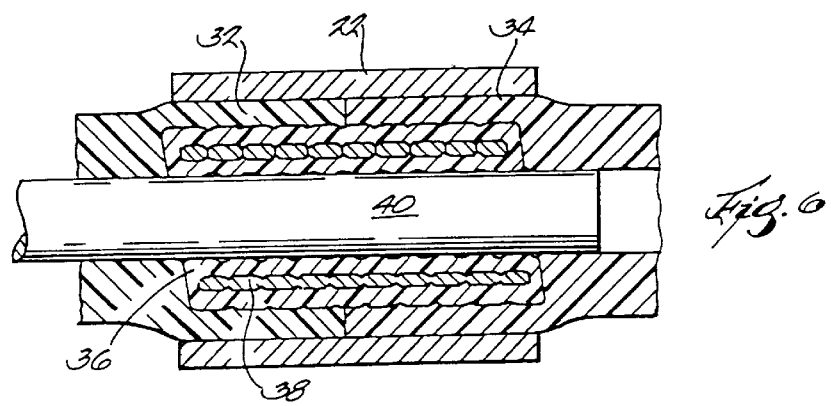
FIG. 6 is a cross-sectional view showing the components of FIG. 5 during the bonding step.
Figure 7:
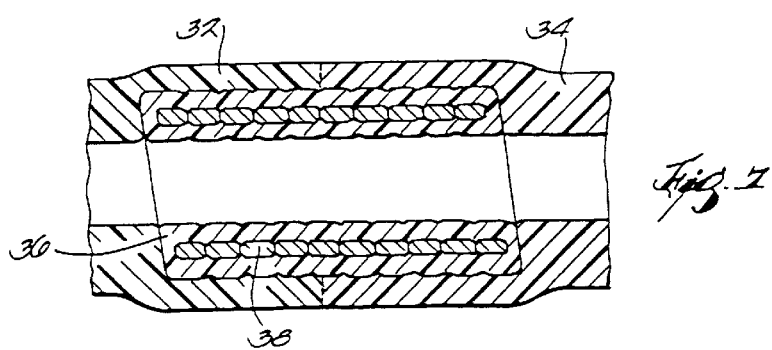
FIG. 7 is a sectional view showing the components of FIG. 5 after bonding; and, FIG. 8 is a perspective view of a heating device usable in connection with the invention.

An alternative embodiment of the invention is shown in FIGS. 5 to 7. In this case, segments 32 and 34 are being bonded together. A sleeve 17 includes a material 36 which, once again, may be, for example, a polyamide polymer. A flat wire 38 is illustrated as being spirally wound between the surfaces of material 36. Again, the cross section of the wire may be round, or any other desired configuration, instead. Although not required in the process of the invention, a central mandril 40 is optionally positioned within the inner diameter of the catheter segments 32 and 34 and tube 36. Mandril 40 may also formed of PTFE.

In order to provide suitable flexibility to the final bonded area, it is preferred that the reinforcing wires 18 or 38 be formed of a metal such as stainless steel or copper clad steel. The very thin preferred cross-section of the sleeves 16 and 17 also insures that flexibility is provided. It is generally preferred that the wall thickness of the sleeve be in the neighborhood of 0.005 inch.

Figure 8:
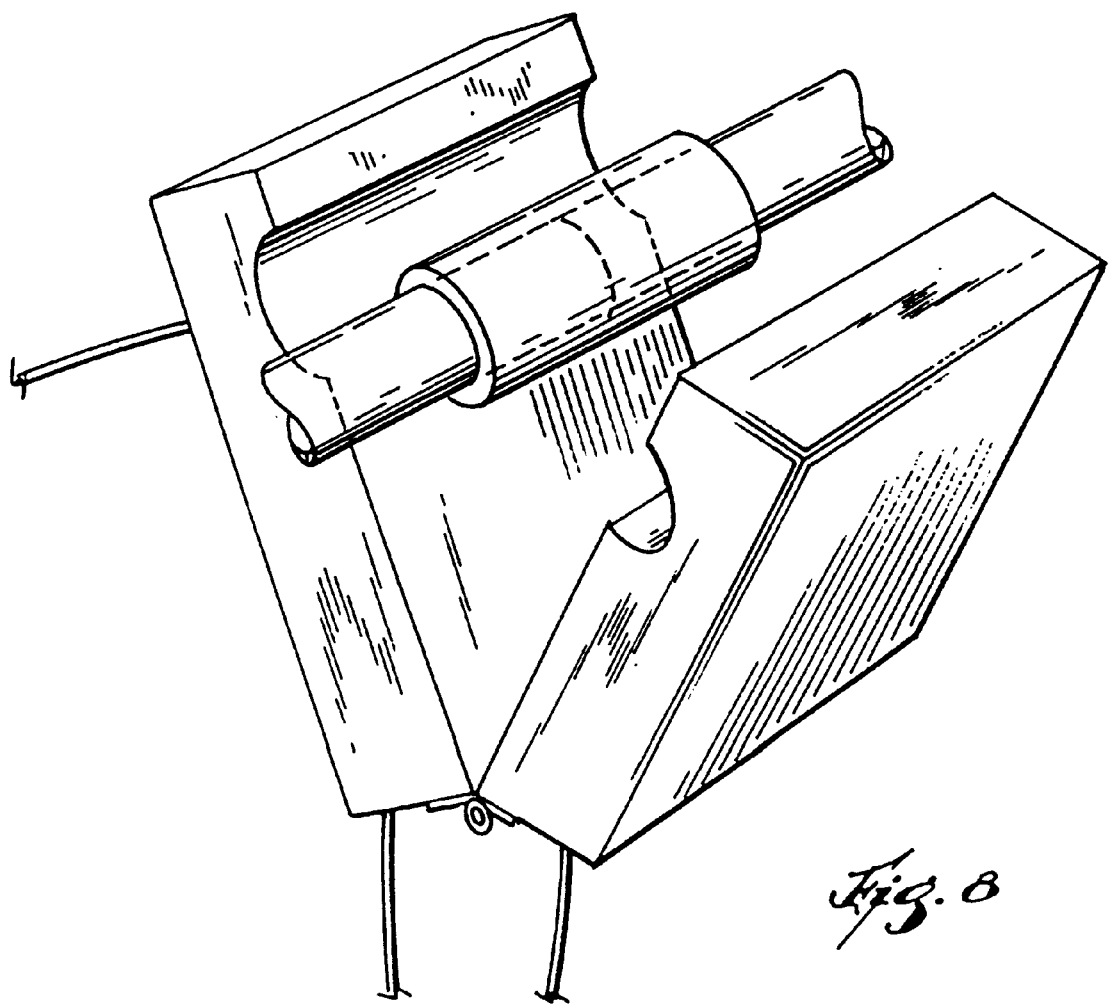

Various heating devices can be used to fuse the catheter materials together. An example is shown in FIG. 8. In FIG. 8 a heating element is formed from two hinged metallic block components 39 and 40. The blocks may be heated by resistance heaters positioned internally and supplied by electrical leads 42 and 44, respectively. A thermocouple is also preferably located within either or both of components 39 and 40 and connected to a temperature monitoring and control circuit by means of a lead 46. Such a control circuit can be used in accordance with known technology to control the temperature of mold blocks 39 and 40 within a desired range of elevated temperatures. Components 39 and 40 are provided with mating semi-cylindrical mold cavities 48 and 50 adapted to fit closely over a capture tube 22.

It has generally been found suitable to heat the sleeve segments to a temperature in the range of about 200° to 450° F., depending on the glass transition temperature of the particular plastic materials being used. Such temperatures have been found to effectively fuse the ends of the catheter segments together without fusion or loss of integrity of the sleeve material. In most cases, a heating interval of about 10 to 20 seconds has been found effective. If temperatures approaching the melting point of the sleeve material are utilized, it is, of course, important that a mandril be utilized in such circumstances.

While preferred embodiments of the invention have been shown for purposes of modification, this will be apparent to those skilled in the art following within the true scope of the appended claims.

What is claimed is:

1. A method of bonding first and second tubing segments together and to a temperature resistant sleeve to form a composite catheter body the temperature resistant sleeve having a polymeric body of material with a melting point which is substantially higher than the melting points of the first and second tubing segment, comprising:

directing the first and second tubing segments together over the temperature resistant sleeve while heating the first and second tubing segments above their melting points but below the melting point of the polymeric body, so that the melting point of the material of the polymeric body is not attained to;

whereby the segments flow together to bond the first and second tubing segments together and to the temperature resistant sleeve to provide a reinforced butt bond.

2. The method of claim 1, wherein the first and second tubing segments are placed within a capture tube while heating the first and second tubing segments.

3. The method of claim 2, wherein the capture tube, with the first and second tubing segments and the polymeric sleeve therein, is placed in a heating element.

4. The method of claim 2, wherein the first and second tubing segments are heated by applying hot air thereto.

5. The method of claim 1, wherein the polymeric sleeve includes a spirally wound reinforcement therein.

6. The method of claim 1, wherein the first and second tubing segments are heated to a temperature of between about 200° F. and 450° F.

7. The method of claim 1, wherein the polymeric sleeve has a melting point of at least about 700° F.

* * * * *